(12) United States Patent
Blacker et al.

(10) Patent No.: US 9,981,109 B2
(45) Date of Patent: May 29, 2018

(54) GUIDE WIRE OR WORKING CATHETER WITH MODIFIED DRIVE SURFACE

(71) Applicant: Corindus, Inc., Waltham, MA (US)

(72) Inventors: Steven J. Blacker, Framingham, MA (US); Christopher Zirps, Sharon, MA (US)

(73) Assignee: CORINDUS, INC., Waltham, MA (US)

( * ) Notice: Subject to any disclaimer, the term of this patent is extended or adjusted under 35 U.S.C. 154(b) by 25 days.

(21) Appl. No.: 14/775,098

(22) PCT Filed: Mar. 14, 2014

(86) PCT No.: PCT/US2014/027836
§ 371 (c)(1),
(2) Date: Sep. 11, 2015

(87) PCT Pub. No.: WO2014/143746
PCT Pub. Date: Sep. 18, 2014

(65) Prior Publication Data
US 2016/0045709 A1    Feb. 18, 2016

Related U.S. Application Data

(60) Provisional application No. 61/818,569, filed on May 2, 2013, provisional application No. 61/790,876, filed on Mar. 15, 2013.

(51) Int. Cl.
*A61M 25/01* (2006.01)
*A61M 25/09* (2006.01)
(Continued)

(52) U.S. Cl.
CPC ..... *A61M 25/0113* (2013.01); *A61B 19/2203* (2013.01); *A61B 34/30* (2016.02);
(Continued)

(58) Field of Classification Search
None
See application file for complete search history.

(56) References Cited

U.S. PATENT DOCUMENTS 4,739,768 A * 4/1988 Engelson .......... A61M 25/0045
600/435
4,769,983 A 9/1988 Stahlecker et al.
(Continued)

FOREIGN PATENT DOCUMENTS

GB    2263641    4/1993
JP    05293175   9/1993
(Continued)

OTHER PUBLICATIONS

International Search Report and Written Opinion for PCT/US2014/027836; dated Oct. 10, 2014; 12 pages.

*Primary Examiner* — Peter A Salamon
(74) *Attorney, Agent, or Firm* — Rathe Lindenbaum LLP

(57) ABSTRACT

An elongated medical device with a modified drive surface for use with the driving mechanism of a robotic system. The elongated medical device has a distal portion configured to navigate the lumen of a human body channel and a proximate portion with a surface different from that of the distal portion and adapted to better interact with the driving mechanism than the surface of the distal portion.

21 Claims, 4 Drawing Sheets

(51) Int. Cl.
  *A61B 19/00* (2006.01)
  *A61M 25/00* (2006.01)
  *A61B 34/30* (2016.01)
  *A61B 90/00* (2016.01)

(52) U.S. Cl.
  CPC ........ *A61M 25/0009* (2013.01); *A61M 25/09* (2013.01); *A61M 25/09041* (2013.01); *A61B 2019/2211* (2013.01); *A61B 2019/5437* (2013.01); *A61B 2019/5454* (2013.01); *A61B 2034/301* (2016.02); *A61B 2090/3937* (2016.02); *A61B 2090/3954* (2016.02); *A61M 25/0021* (2013.01); *A61M 25/0045* (2013.01); *A61M 2025/006* (2013.01); *A61M 2025/09108* (2013.01); *A61M 2025/09133* (2013.01)

(56) References Cited

U.S. PATENT DOCUMENTS

| | | | |
|---|---|---|---|
| 5,095,915 A * | 3/1992 | Engelson | A61M 25/09 600/434 |
| 5,147,317 A | 9/1992 | Shank et al. | |
| 5,219,361 A * | 6/1993 | von Recum | A61F 2/0077 623/23.74 |
| 5,379,779 A | 1/1995 | Rowland et al. | |
| 5,437,288 A | 8/1995 | Schwartz et al. | |
| 5,497,785 A | 3/1996 | Viera | |
| 5,779,623 A * | 7/1998 | Bonnell | A61B 90/50 414/431 |
| 5,957,941 A * | 9/1999 | Ream | A61B 8/12 600/443 |
| 6,027,460 A | 2/2000 | Shturman | |
| 6,110,192 A * | 8/2000 | Ravenscroft | A61M 25/1002 604/103.08 |
| 6,246,200 B1 * | 6/2001 | Blumenkranz | B25J 9/1689 128/DIG. 7 |
| 6,319,227 B1 * | 11/2001 | Mansouri-Ruiz | A61B 8/4461 600/466 |
| 6,398,755 B1 * | 6/2002 | Belef | A61B 8/12 604/95.01 |
| 6,468,265 B1 * | 10/2002 | Evans | A61B 34/32 600/103 |
| 6,514,261 B1 * | 2/2003 | Randall | A61F 2/95 604/528 |
| 6,522,909 B1 * | 2/2003 | Garibaldi | A61B 5/062 128/899 |
| 6,533,770 B1 * | 3/2003 | Lepulu | A61M 25/0012 604/264 |
| 6,636,758 B2 | 10/2003 | Sanchez et al. | |
| 6,684,129 B2 * | 1/2004 | Salisbury, Jr. | B25J 3/00 128/897 |
| 6,726,675 B1 * | 4/2004 | Beyar | A61M 25/0105 600/106 |
| 7,413,565 B2 * | 8/2008 | Wang | G06F 19/3418 606/1 |
| 7,687,144 B2 | 3/2010 | Clark et al. | |
| 7,887,549 B2 * | 2/2011 | Wenderow | A61M 25/0113 600/585 |
| 2001/0049549 A1 * | 12/2001 | Boylan | A61F 2/95 623/1.11 |
| 2002/0013549 A1 | 1/2002 | Zhong et al. | |
| 2005/0021015 A1 * | 1/2005 | Keidar | A61B 17/2202 606/27 |
| 2006/0146010 A1 * | 7/2006 | Schneider | A61M 25/0105 345/156 |
| 2008/0064920 A1 * | 3/2008 | Bakos | A61B 1/00133 600/102 |
| 2009/0054875 A1 | 2/2009 | Strauss et al. | |
| 2009/0247942 A1 * | 10/2009 | Kirschenman | A61M 25/0147 604/95.04 |
| 2009/0299459 A1 | 12/2009 | Lentz | |
| 2009/0326449 A1 * | 12/2009 | Wang | A61M 25/09041 604/95.01 |
| 2010/0021619 A1 | 1/2010 | Osborne et al. | |
| 2010/0049169 A1 | 2/2010 | Noriega et al. | |
| 2010/0069833 A1 * | 3/2010 | Wenderow | A61M 25/0113 604/95.01 |
| 2010/0130987 A1 * | 5/2010 | Wenderow | A61M 25/0113 606/130 |
| 2010/0222669 A1 * | 9/2010 | Flickinger | A61M 25/01 600/424 |
| 2010/0305394 A1 | 12/2010 | Rosenblatt | |
| 2011/0015484 A1 * | 1/2011 | Alvarez | A61B 1/307 600/109 |
| 2011/0028941 A1 * | 2/2011 | Nagano | A61B 17/12022 604/528 |
| 2011/0238010 A1 * | 9/2011 | Kirschenman | A61M 25/0105 604/95.04 |
| 2012/0179167 A1 * | 7/2012 | Wenderow | A61B 34/30 606/130 |
| 2013/0274657 A1 * | 10/2013 | Zirps | A61M 25/0113 604/95.01 |

FOREIGN PATENT DOCUMENTS

| | | | | |
|---|---|---|---|---|
| WO | | 1993018817 A1 | 9/1993 | |
| WO | WO | 2012037213 A1 * | 3/2012 | ........ A61M 25/0113 |

* cited by examiner

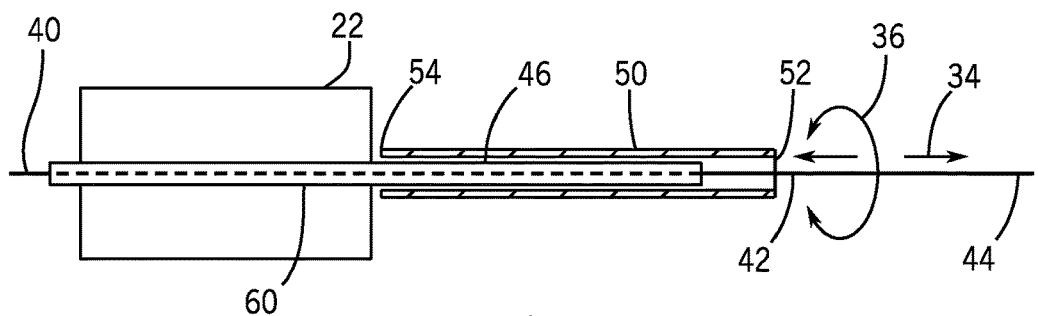
FIG. 2B
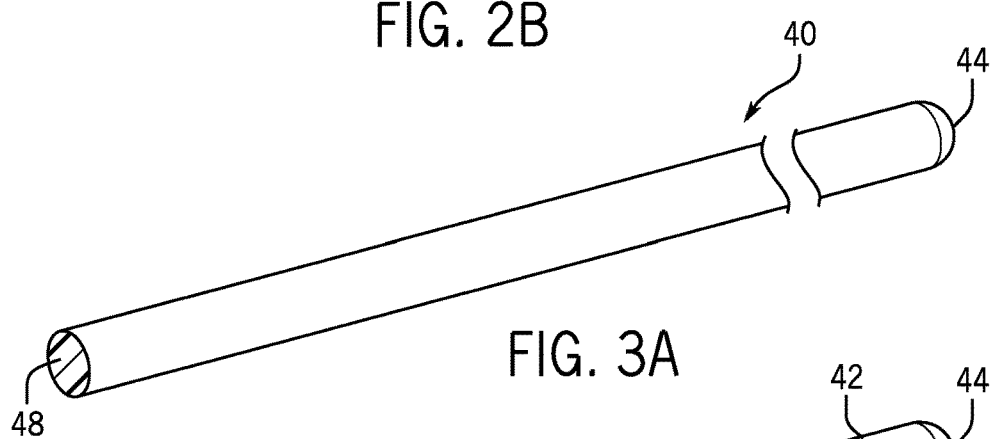
FIG. 3A
FIG. 3B
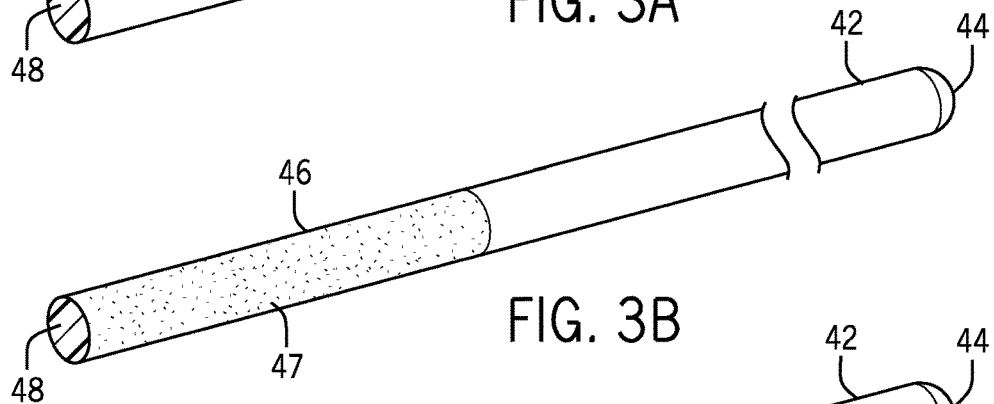
FIG. 3C
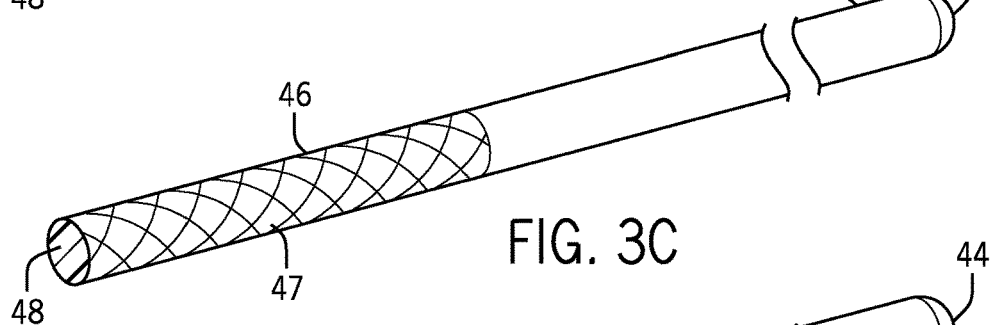
FIG. 3D
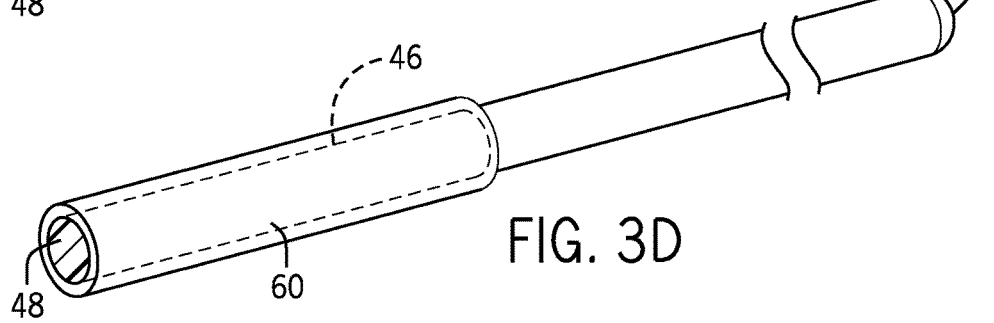

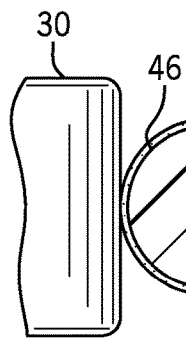
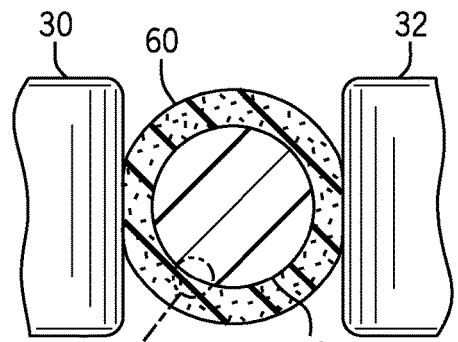
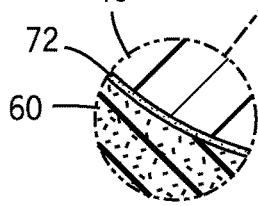
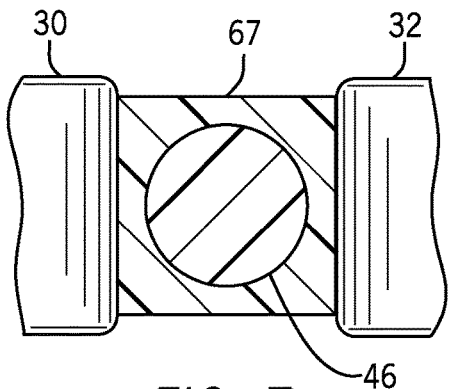
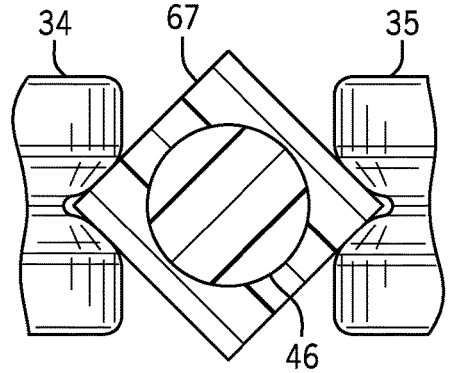
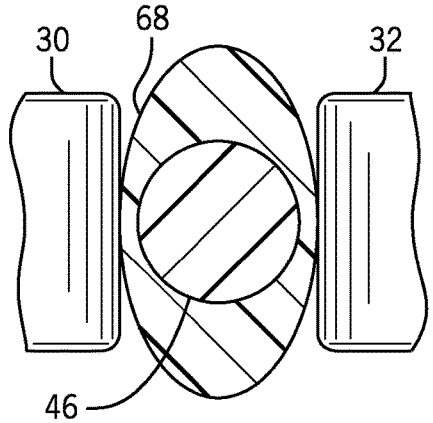
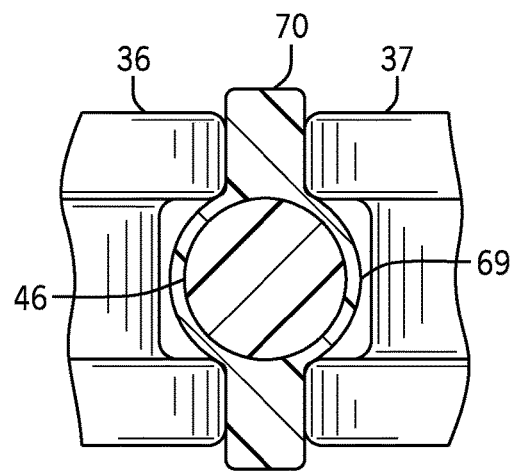

GUIDE WIRE OR WORKING CATHETER WITH MODIFIED DRIVE SURFACE

BACKGROUND

Guide wires are used to facilitate percutaneous procedures in which the guide wire and often guide and working catheters are threaded into a human patient using X-ray guidance. The guide wires are manually threaded by a physician or other medical personnel but this requires that the operator be adjacent to the patient and so be in the immediate vicinity of the X-ray radiation providing the image used for guidance. Systems have been developed, such as that disclosed in U.S. Pat. No. 7,887,549 incorporated herein by reference, which allow the guide wires and catheters to be threaded into the patient robotically and thus allow the user or operator to be remote from the patient and the X-ray radiation. However, this involves the guide wire being mechanically, as opposed to manually, driven. Thus there is a concern about the interaction between the surface of the guide wire and the driving mechanism of the robotic system which may involve drive wheels and idler wheels because the surface of the guide wire has been optimized for passage through the interior of the human body. Therefore it may have a somewhat slippery surface which is not optimum for interaction with the drive mechanism. This is also the case for robotically driven catheters. In addition the surface of the guide wire or catheter may be subject to damage or injury from its interaction with the drive mechanism, particularly when the drive mechanism involves wheels which apply a pinch force.

SUMMARY

In one embodiment an elongated medical device with a modified drive surface for use with the driving mechanism of a robotic system. The elongated medical device has a distal portion configured to navigate the lumen of a human body channel and a proximate portion with a surface different from that of the distal portion and adapted to better interact with the driving mechanism than the surface of the distal portion.

The present invention also involves a method of modifying a guide wire or working catheter, with a distal portion configured to navigate the lumen of a human body channel, to enhance its interaction with the driving mechanism of a robotic system. A sleeve with a surface different from that of the distal portion and adapted to better interact with the driving mechanism than the surface of the distal portion is positioned over the proximate portion of the guide wire or working catheter such that it does not enclose the distal portion. Then the sleeve is caused to shrink in the radial direction such that it firmly engages the guide wire or working catheter.

BRIEF DESCRIPTION OF THE DRAWINGS

FIG. 2B is a top cross sectional view of a guide wire with a modified proximate portion passing out of the drive mechanism and into and out of a guide catheter.

FIG. 3A is a perspective view of a guide wire.

FIG. 3B is a perspective view of a guide wire with a proximate portion with a modified surface.

FIG. 3C is a perspective view of a guide wire with a proximate portion with a surface carrying a pattern.

FIG. 3D is a perspective view of a guide wire with a proximate portion with a surface carrying a sleeve.

FIG. 5 is an axial cross section of the proximate portion of a guide wire between the wheels of a drive mechanism with a modified surface.

FIG. 6 is an axial cross section of the proximate portion of a guide wire between the wheels of a drive mechanism with a surrounding sleeve.

FIG. 7 is an axial cross section of the proximate portion of a guide wire between the wheels of a drive mechanism with a surrounding sleeve with a square outer surface.

FIG. 8 is an axial cross section of the proximate portion of a guide wire between specially adapted wheels of a drive mechanism with a surrounding sleeve with a square outer surface.

FIG. 9 is an axial cross section of the proximate portion of a guide wire between the wheels of a drive mechanism with a surrounding sleeve with an oval outer surface.

FIG. 10 is an axial cross section of the proximate portion of a guide wire between the wheels of a drive mechanism with a surrounding sleeve with wings projecting from its outer surface.

DETAILED DESCRIPTION

Figure 1:
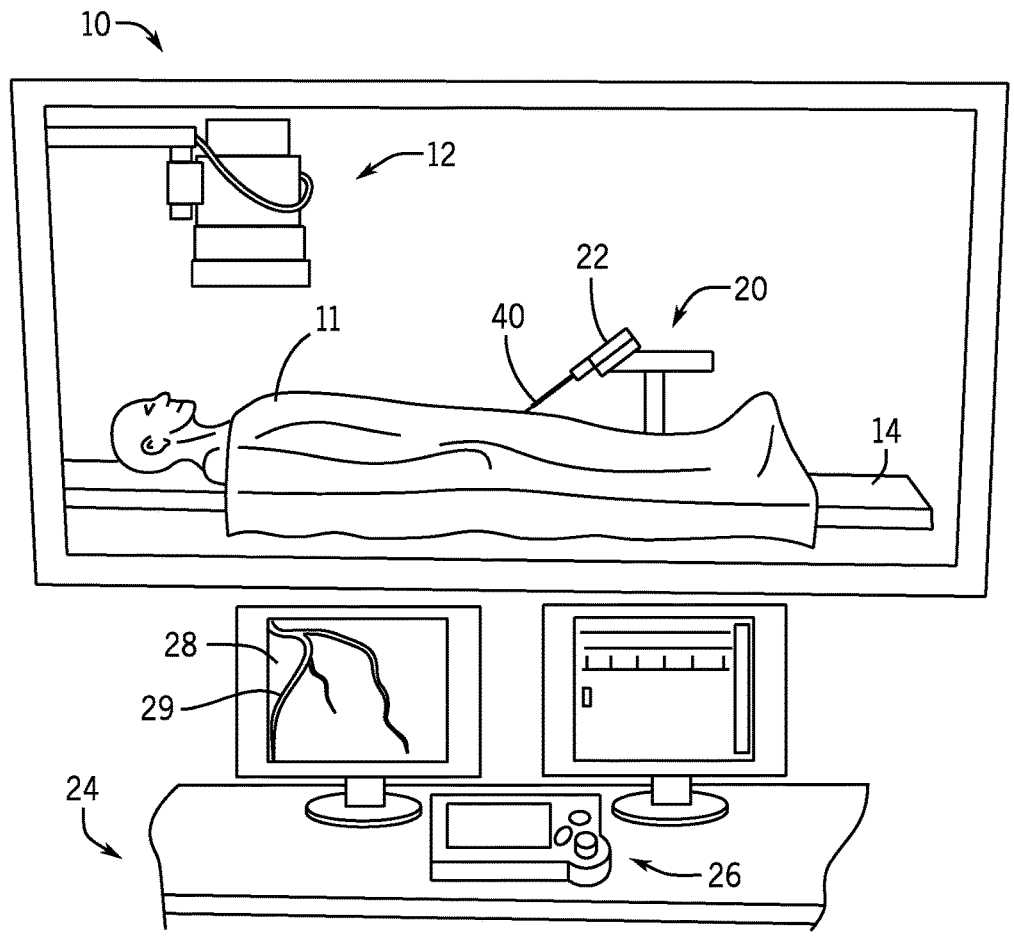
FIG. 1 is a perspective view of the environment in which a robotic system for driving a guide wire or working catheter in a percutaneous intervention procedure involving a human patient operates.

Referring to FIG. 1, one embodiment involves a system for performing percutaneous intervention procedures on human patients in a cath lab 10 in which an X-ray system 12 is used to monitor the procedure involving the patient 11 on the patient table 14. A robotic system 20 with a drive mechanism 22 is used to feed a guide wire 40 or working catheter and its progress is controlled and monitored from a remote console 24 that has a control panel 26 and a display 28 which is fed an image from the X-ray system 12.

Figure 2A:
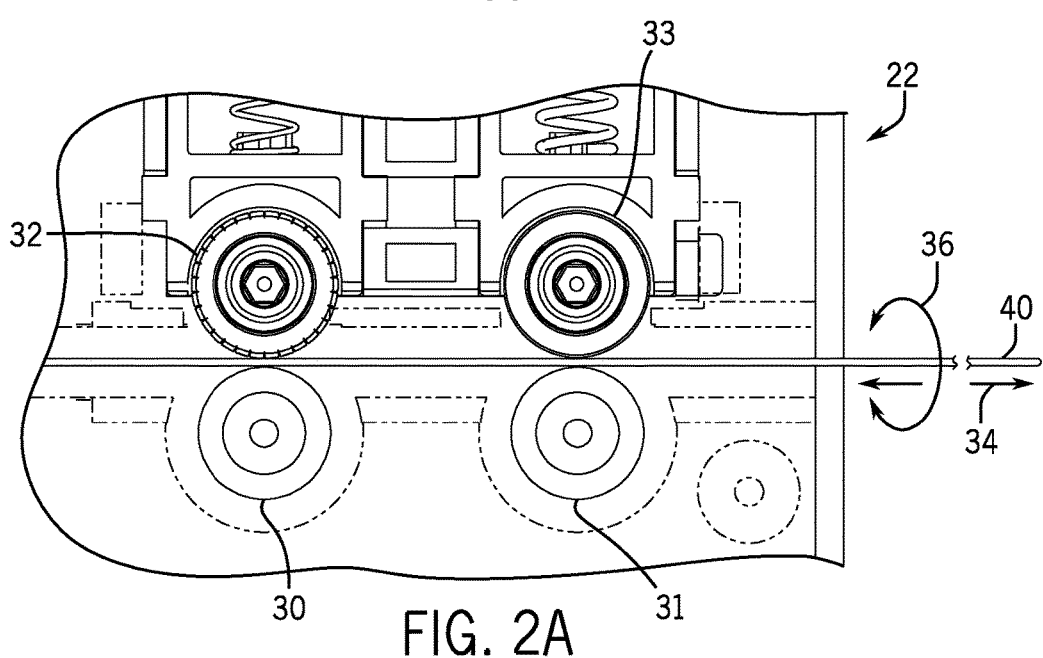
FIG. 2A is a top elevation of the drive mechanism of the robotic system.

Referring to FIG. 2A, one embodiment involves a drive mechanism 22 that uses a drive wheel 30 and an idler wheel 32 to impart axial motion 34 to a guide wire 40. The drive mechanism also imparts rotational motion 36 to the guide wire 40. The drive mechanism 22 also includes a measurement wheel 31 and its idler 33. The measurement wheel 31 is linked to a mechanism (not displayed), such a magnetic rotation measurement mechanism, which provides a measure of the axial motion of the guide wire 40. The accuracy of this measurement is dependent on the interaction of the guide wire 40 with the measurement wheel 31 and can be compromised by slippage between the two.

Referring to FIG. 2B, one embodiment involves a drive mechanism 22 that feeds a guide wire 40 into a guide catheter 50 which has typically been manually threaded into a blood vessel, such as the femoral artery, of a patient. Guide Catheter 50 has a distal end 52, and a proximate end 54. The guide wire 40 has a distal portion 42, which terminates in a tip 44 which may have an arcuate shape or other profile proximate the tip 44, and a proximate portion 46, which interacts with the driving mechanism 22. The distal portion 42 is designed to navigate the lumen of the blood vessel and has the appropriate lubricity and flexibility to do so. It has the appropriate length to reach from the distal end 52 of the guide catheter 50 to a location of interest within a patient. The proximate portion 46 has been provided with a sleeve 60 which facilitates its interaction with the drive mechanism 22 to impart both axial motion 34 and rotational motion 36 to the guide wire 40. Note FIG. 2A and FIG. 2B are schematic. The guide catheter 50 may be of the type that may be supported by a drive mechanism as disclosed in U.S. Pat. No. 7,887,549 entitled Catheter System. The Figures are not meant to be to scale and are for illustrative purposes only. For example the length of the guide catheter 50 and guide wire 40 may be longer than illustrated.

Referring to FIG. 3A, one embodiment involves the modification of a guide wire 40 that has a tip 44 at its distal end and has a proximate terminus 48. In one embodiment a guide wire as obtained from a supplier that may have along its entire length from the tip 44 to the proximate terminus 48 a certain lubricity and flexibility appropriate to navigate the lumen of a blood vessel.

Referring to FIG. 3B, one embodiment involves the modification of a guide wire 40 by applying a treatment, such as a chemical or laser etch, which causes the surface 47 of its proximate portion 46 to have a higher coefficient of friction than the untreated surface and thus to interact with the drive mechanism 22 to facilitate axial movement 34 and rotational movement 36.

Referring to FIG. 3C, one embodiment involves the modification of a guide wire 40 by applying a pattern, such as ridges angled at 45° to the axis, to the surface 47 of its proximate portion 46. The pattern interacts with the drive mechanism 22 to facilitate axial movement 34 and rotational movement 36.

Referring to FIG. 3D, one embodiment involves the modification of a guide wire 40 by covering its proximate portion 46 with a sleeve 60. The pattern interacts with the drive mechanism 22 to facilitate axial movement 34 and rotational movement 36.

Figure 4A:
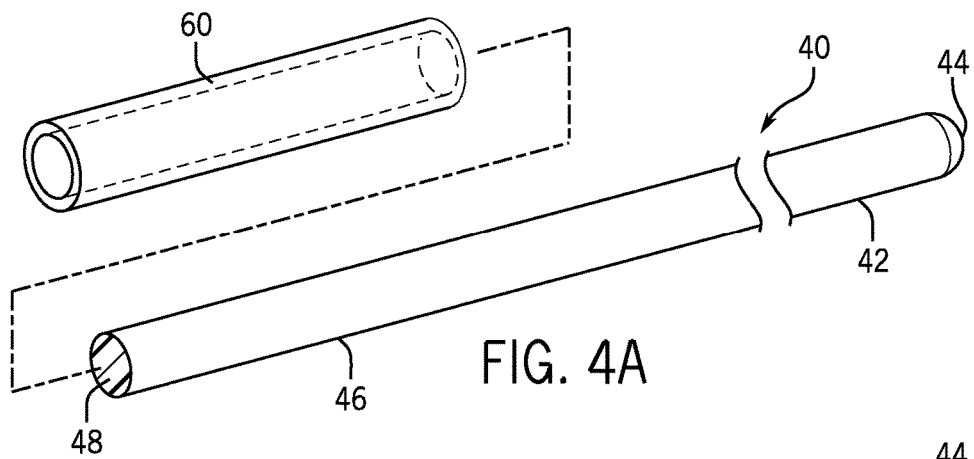
FIG. 4A is a perspective view of a sleeve being applied over the terminal end of a guide wire.

Referring to FIG. 4A, one embodiment involves the modification of a guide wire 40 by sliding a sleeve 60 over its proximate terminus 48 or inserting this end 48 into the sleeve 60 so as to cover the proximate portion 46. This avoids the risk of damaging or altering the tip 44 and the distal portion 42 and thereby affecting their ability to readily navigate the lumen of a blood vessel.

Figure 4B:
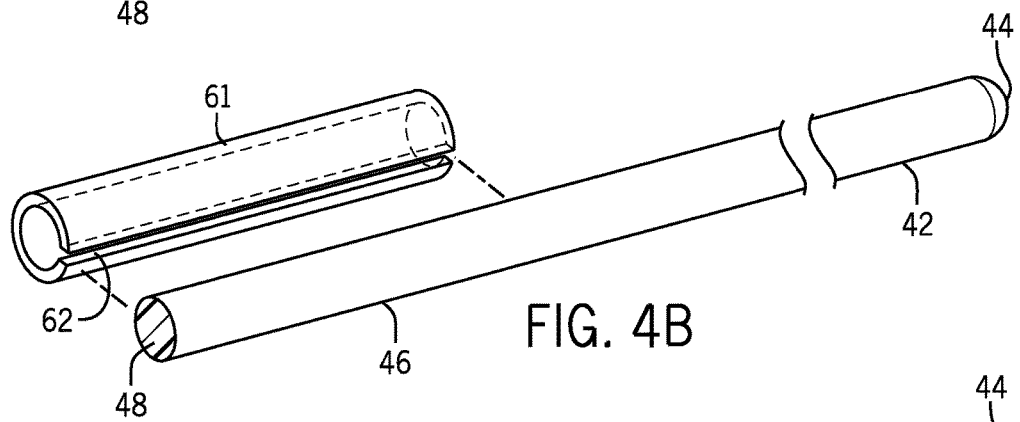
FIG. 4B is a perspective view of a sleeve being applied over the proximate portion of a guide wire.

Referring to FIG. 4B, one embodiment involves the modification of a guide wire 40 by using a sleeve 61 with an axial slit 62 to cover the proximate portion 46.

Figure 4C:
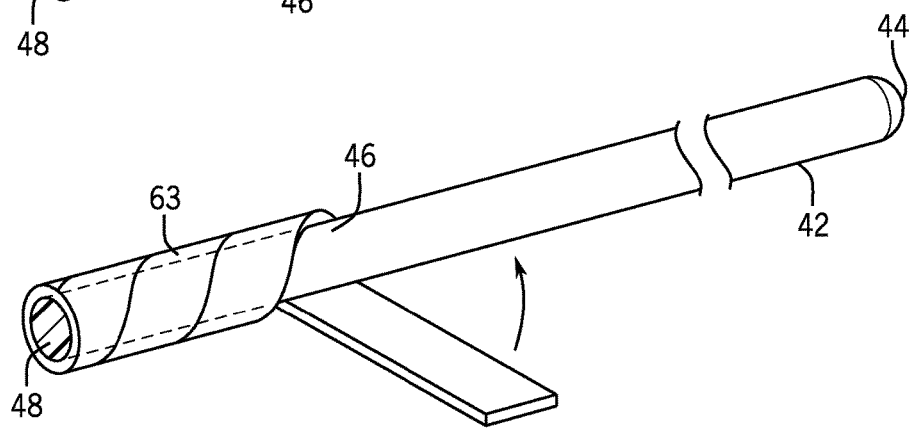
FIG. 4C is a perspective view of a sleeve being applied by wrapping over the proximate portion of a guide wire.

Referring to FIG. 4C, one embodiment involves the modification of a guide wire 40 by wrapping a rectangular strip 63 around the proximate portion 46 using a spiral wrapping pattern.

Figure 4D:
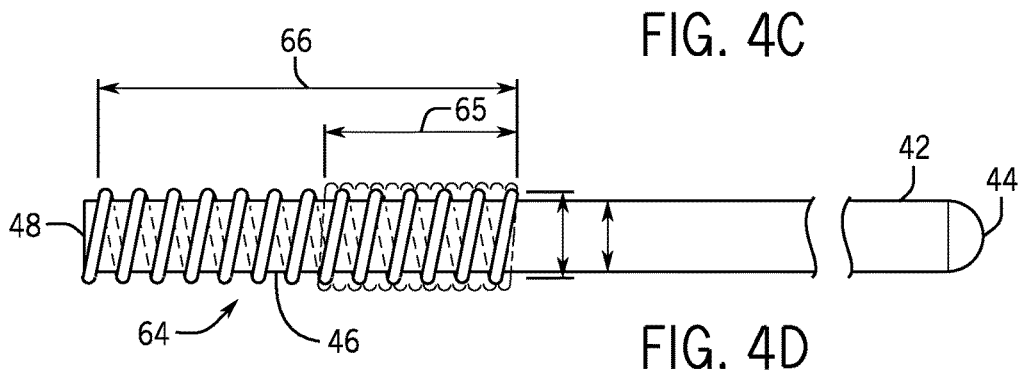
FIG. 4D is a perspective view of a helical coil sleeve being applied to the proximate portion of a guide wire.

Referring to FIG. 4D, one embodiment involves the modification of a guide wire 40 by placing the proximate portion inside of a helical coil 64 while it is in an axially compressed state 65 and then releasing the compression. In the relaxed state 66 the coil 64 assumes a configuration with a smaller inside radius that firmly grasps the proximate portion 46.

Referring to FIG. 5, in the embodiment involving the surface modification 47, its interaction with the drive wheel 30 and its idler wheel 32 can be seen. It is the modified surface 47 that contacts the surfaces of these two wheels.

Referring to FIG. 6, in the embodiment involving the sleeve 60, its interaction with the drive wheel 30 and its idler wheel 32 can be seen. It is the sleeve 60 that contacts the surfaces of these two wheels. The sleeve 60 may be conveniently affixed to the proximate portion 46 with a pressure sensitive adhesive 72.

Referring to FIG. 7, a sleeve 67 with a square cross section has been affixed to the proximate portion 46. Not only does this provide more surface area for interaction with the drive wheel 30 and its idler 32 in axial motion, but it also enhances the interaction to impart rotational motion 36.

Referring to FIG. 8, a modified drive wheel 34 and its idler 35 have been provided to interact with the sleeve 67.

Referring to FIG. 9, a sleeve 68 with an oval cross section has been affixed to the proximate portion 46. Not only does this provide more surface area for interaction with the drive wheel 30 and its idler 32 in axial motion, but it also enhances the interaction to impart rotational motion 36.

Referring to FIG. 10, a sleeve 69 with wings 70 has been affixed to the proximate portion 46 and combined with a modified drive wheel 36 and its idler 37. The wings 70 are quite helpful in imparting rotational motion 36 to the guide wire 40.

The proximate portion 46 of a guide wire or working catheter may be modified in a variety of ways to enhance its interaction with the drive mechanism 22 of the robotic system 20. In some embodiments its surface is modified to have a significantly higher coefficient of friction than the distal portion 42. In one embodiment its surface is imparted a pattern of ridges and valleys. In another embodiment it is given a non-circular cross section, for instance by the application of a sleeve.

The various sleeves 60, 61, 63, 67, 68 and 69 can be adhered to the proximate portion in a variety of ways. They can be constructed of a material, such as certain types of polymers that shrink in the radial direction when exposed to appropriate conditions, such as heat or appropriate radiation, such as ultraviolet light. It is convenient if these conditions, particularly the heat, are such that they do not pose a risk of damaging or modifying the distal portion 42. They can also be constructed of materials that shrink in the radial direction when stretched in the axial direction. Another approach is to interpose a pressure sensitive coating between the surface of the proximate portion 46 and the interior surface of the sleeve.

The sleeves conveniently have a circular interior cavity to accommodate the typical guide wire or working catheter that typically has a circular cross section. However, in some embodiments the exterior surface of the sleeve is non-circular. One embodiment involves a sleeve with a cross section with wings located opposite each other and extending radially outward from an otherwise generally circular cross section.

There are a wide variety of surface modifications and methods of applying them to the surface of the proximate portion of the guide wire or working catheter so that it better interacts with the drive mechanism of a robotic system. The material out of which the guide wire or working catheter is constructed may allow some types of modification while others may be facilitated by the use of a sleeve. This surface may be subjected to a chemical, laser or plasma etch. It may be modified by providing it with a grip, extra friction or nano coating. Because the entire surface of a guide wire or working catheter may be adapted to navigating the lumen of a human body channel such as a blood vessel, it typically already carries a coating which imparts high lubricity and coating its proximate portion to better interact with the driving mechanism of a robotic system may involve first removing this original coating. The surface of proximate portion may be given a design pattern such as spirals, a circumferential tread or ridges angled at 45 degrees to this portions axis. This surface may be provided with a tread pattern. This surface may also be adapted to interact with particular drive wheels forming part of the drive mechanism such as polyurethane wheels.

The surface modification of the proximate portion may also be used to better monitor and control the movement of the guide wire or working catheter. This surface may be provided optical or magnetic markers or a grid which can be read by appropriate sensors such as a torque sensor to monitor the rotation and advancement of the guide wire or working catheter. The markers may be so configured such that any torque in the guide wire or working catheter may be readily determined and potentially used in instructing the drive mechanism. For instance, the surface may be given a pattern which becomes skewed when the guide wire or working catheter is subjected to torque and appropriate sensors provided to read this skewness. In one embodiment a sensor may detect twisting of the elongated device about its longitudinal axis by movement of the pattern or optical markers or magnetic markers on the elongated medical device In order to avoid effecting the original surface of the distal portion of the guide wire or working catheter, so that it retains its originally designed ability to readily navigate the lumen of a human body channel, the treatment of the proximate portion be effected from its proximate terminus. For instance, if a sleeve approach is used the sleeve may be slipped over this terminus and not advanced axially so far as to enclose the distal portion.

The guide wire or working catheter with a modified proximate surface conveniently has a distal portion which has been imparted a lubricity and flexibility which optimizes its ability to navigate the lumen of a human blood vessel.

One embodiment involves the modified guide wire or working catheter with a guide catheter. In one embodiment the lengths of the proximal and distal portions have been optimized such that when the guide catheter is in place and the guide wire or working catheter is advanced to the site of action (area proximate a lesion) only the distal portion projects beyond the end of the guide catheter.

One embodiment involves combining the modified guide wire or working catheter with a guide catheter and a remotely controlled drive mechanism for advancing a guide wire or working catheter into a lumen of a human blood vessel. In one embodiment the guide wire or working catheter has been modified to have a proximate portion which has a higher coefficient of friction than its distal portion and the lengths of the two portions are such that when the guide catheter is in place and the guide wire or working catheter is advanced to the site of action only the distal portion projects beyond the end of the guide catheter adjacent to the site of action and the proximate portion extends back to the driving mechanism.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. Any of the features, elements, or components of any of the exemplary embodiments discussed above may be used alone or in combination with any of the features, elements, or components of any of the other embodiments discussed above. It is to be understood that the forms of the invention shown and described herein are to be taken as presently preferred embodiments. Elements and materials may be substituted for those illustrated and described herein, parts and processes may be reversed, and certain features of the invention may be utilized independently, all as would be apparent to one skilled in the art having the benefit of this description of the invention. Changes may be made in the elements described herein without departing form the spirit and scope of the invention as described in the following claims.

What is claimed is:

1. A robotic percutaneous procedure system comprising:
   a remotely controlled drive mechanism for advancing a guide wire or working catheter into a channel of the human body;
   a guide catheter which is placed in the human body channel; and
   a guide wire or working catheter having:
      a distal portion configured to navigate the lumen of a human body channel;
      a proximate portion with a surface different from that of the distal portion and adapted to better interact with the driving mechanism than the surface of the distal portion; and
      a length sufficient to extend from the drive mechanism to beyond the end of the guide catheter which is distal from the drive mechanism, with the length of the proximal portion being such that it does not extend out of the guide catheter when the distal portion has reached its farthest extension into the human body channel;
   wherein the proximate portion surface includes at least one of optical or magnetic markers.

2. The system of claim 1 wherein the drive mechanism, guide catheter and the distal portion of the guide wire or working catheter are adapted for use in a human blood vessel.

3. The system of claim 1 wherein the surface of the proximate portion has been modified to have a higher coefficient of friction than the surface of the distal portion.

4. A method of modifying a guide wire or working catheter, with a distal portion configured to navigate the lumen of a human body channel, to enhance its interaction with the driving mechanism of a robotic system comprising:
   positioning a sleeve with a surface different from that of the distal portion and adapted to better interact with the driving mechanism than the surface of the distal portion over a proximate portion of the guide wire or working catheter such that it does not enclose the distal portion; and
   causing the sleeve to shrink in the radial direction such that it firmly engages the guide wire or working catheter.

5. The method of claim 4 wherein the sleeve is slipped over the proximate portion beginning at a proximate terminus of the proximate portion.

6. The method of claim 4 wherein the sleeve has an axial slit and the proximal portion is passed through this slit to the bore of the sleeve.

7. A robotic percutaneous procedure system comprising:
   a remotely controlled drive mechanism for advancing a guide wire or working catheter into a channel of the human body;
   a guide catheter which is placed in the human body channel; and
   a guide wire or working catheter having:
      a distal portion configured to navigate the lumen of a human body channel;

a proximate portion with a surface different from that of the distal portion and adapted to better interact with the driving mechanism than the surface of the distal portion; and a length sufficient to extend from the drive mechanism to beyond the end of the guide catheter which is distal from the drive mechanism, with the length of the proximal portion being such that it does not extend out of the guide catheter when the distal portion has reached its farthest extension into the human body;

wherein the proximate portion surface includes a grid which can be read by a sensor to monitor the rotation and advancement of the guide wire or working catheter.

8. The robotic percutaneous procedure system of claim 7, wherein the grid on the proximate portion surface becomes skewed when the guide wire or working catheter is subjected to torque.

9. The robotic percutaneous procedure system of claim 1 wherein the proximate portion surface has been modified to have a higher coefficient of friction than the distal portion.

10. The robotic percutaneous procedure system of claim 9 wherein the surface of the proximate portion has been modified to have a pattern of ridges and valleys.

11. A robotic percutaneous procedure system comprising:
a remotely controlled drive mechanism for advancing a guide wire or working catheter into a channel of the human body;
a guide catheter which is placed in the human body channel; and
a guide wire or working catheter having:
    a distal portion configured to navigate the lumen of a human body channel;
    a proximate portion with a surface different from that of the distal portion and adapted to better interact with the driving mechanism than the surface of the distal portion; and
    a length sufficient to extend from the drive mechanism to beyond the end of the guide catheter which is distal from the drive mechanism, with the length of the proximal portion being such that it does not extend out of the guide catheter when the distal portion has reached its farthest extension into the human body channel;
    wherein the distal portion has a circular cross section and the proximate portion has a non-circular cross section.

12. The robotic percutaneous procedure system of claim 11 wherein the proximate portion has a cross section with wings located opposite each other and extending radially outward from an otherwise generally circular cross section.

13. A robotic percutaneous procedure system comprising:
a remotely controlled drive mechanism for advancing a guide wire or working catheter into a channel of the human body;
a guide catheter which is placed in the human body channel; and
a guide wire or working catheter having:
    a distal portion configured to navigate the lumen of a human body channel;
    a proximate portion with a surface different from that of the distal portion and adapted to better interact with the driving mechanism than the surface of the distal portion; and
    a length sufficient to extend from the drive mechanism to beyond the end of the guide catheter which is distal from the drive mechanism, with the length of the proximal portion being such that it does not extend out of the guide catheter when the distal portion has reached its farthest extension into the human body channel;
    wherein the surface of the proximate portion has been provided by a sleeve which has been adhered to the surface of the guide wire or working catheter.

14. The robotic percutaneous procedure system of claim 13 wherein the sleeve is constructed of a material which shrinks in the radial direction upon the application to it of heat, radiation or an axial force.

15. The robotic percutaneous procedure system of claim 14 wherein the sleeve is constructed of a polymeric material which shrinks at temperature which is tolerated by the guide wire or working catheter without impairment.

16. The robotic percutaneous procedure system of claim 13 wherein the sleeve is constructed of a helical coil which can be compressed in the axial direction to have a larger inner diameter and has been released from such compression to firmly grasp the guide wire or working catheter.

17. The robotic percutaneous procedure system of claim 1 wherein the surface of the proximate portion has been provided by mechanical or chemical modification of the surface of the guide wire or working catheter.

18. The robotic percutaneous procedure system of claim 17 wherein the surface of the proximate portion has been modified to have a greater coefficient of friction than the surface of the distal portion by etching of the guide wire or working catheter with a laser.

19. The robotic percutaneous procedure system of claim 1, wherein the length has been optimized to extend from the drive mechanism into a human heart via a femoral artery and have only the distal portion extend outside of a properly placed guide catheter.

20. The robotic percutaneous procedure system of claim 1 wherein the remotely controlled drive mechanism includes a drive member.

21. The robotic procedure system of claim 20, wherein the drive member includes a pair of wheels contacting the proximal portion of the guide wire or working catheter.

* * * * *